(12) United States Patent
Dutzmann et al.

(10) Patent No.: US 9,445,601 B2
(45) Date of Patent: *Sep. 20, 2016

(54) FUNGICIDE ACTIVE SUBSTANCE COMBINATIONS

(71) Applicant: Bayer Intellectual Property GmbH, Monheim (DE)

(72) Inventors: Stefan Dutzmann, Langenfeld (DE); Klaus Stenzel, Dusseldorf (DE); Manfred Jautelat, Burscheid (DE)

(73) Assignee: Bayer Intellectual Property GmbH, Monheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/467,653

(22) Filed: Aug. 25, 2014

(65) Prior Publication Data

US 2014/0364469 A1   Dec. 11, 2014

Related U.S. Application Data

(60) Continuation of application No. 13/742,052, filed on Jan. 15, 2013, now Pat. No. 8,846,738, which is a continuation of application No. 09/843,396, filed on Apr. 26, 2001, now abandoned, which is a division of application No. 09/402,866, filed as application No. PCT/EP98/01986 on Apr. 6, 1998, now Pat. No. 6,306,850.

(30) Foreign Application Priority Data

Apr. 18, 1997 (DE) .................................. 197 16 257

(51) Int. Cl.

| | | |
|---|---|---|
| A01N 43/653 | (2006.01) |
| A01N 47/32 | (2006.01) |
| A01N 47/04 | (2006.01) |
| A01N 37/38 | (2006.01) |
| A01N 47/14 | (2006.01) |
| A01N 51/00 | (2006.01) |
| A01N 47/10 | (2006.01) |
| A01N 47/12 | (2006.01) |
| A01N 37/24 | (2006.01) |
| A01N 37/50 | (2006.01) |
| A01N 43/36 | (2006.01) |
| A01N 37/34 | (2006.01) |
| A01N 43/54 | (2006.01) |
| A01N 43/30 | (2006.01) |

(Continued)

(52) U.S. Cl.

CPC .............. *A01N 57/12* (2013.01); *A01N 37/18* (2013.01); *A01N 37/20* (2013.01); *A01N 37/22* (2013.01); *A01N 37/24* (2013.01); *A01N 37/34* (2013.01); *A01N 37/38* (2013.01); *A01N 37/50* (2013.01); *A01N 43/30* (2013.01); *A01N 43/36* (2013.01); *A01N 43/38* (2013.01); *A01N 43/54* (2013.01); *A01N 43/653* (2013.01); *A01N 43/82* (2013.01); *A01N 43/84* (2013.01); *A01N 43/88* (2013.01); *A01N 47/04* (2013.01); *A01N 47/10* (2013.01); *A01N 47/12* (2013.01); *A01N 47/14* (2013.01); *A01N 47/32* (2013.01); *A01N 51/00* (2013.01); *A01N 53/00* (2013.01); *A01N 55/02* (2013.01)

(58) Field of Classification Search
None
See application file for complete search history.

(56) References Cited

U.S. PATENT DOCUMENTS

| | | |
|---|---|---|
| 3,903,090 A | 9/1975 | Fujinami et al. |
| 3,912,752 A | 10/1975 | Meiser et al. |

(Continued)

FOREIGN PATENT DOCUMENTS

| | | |
|---|---|---|
| DE | 19602095 A1 | 7/1997 |
| GB | 2 262 037 A | 6/1993 |

(Continued)

OTHER PUBLICATIONS

The Pesticide Manual, 9th edition, pp. 206, 207, 249, 431, 432, 461, 462, 491, 529-532, 554, 555, 654, 726, 827, 866 and 867, The British Crop Protection Council, Farnham, Surrey, United Kingdom (1991).

(Continued)

*Primary Examiner* — Abigail Fisher
*Assistant Examiner* — Frank Choi
(74) *Attorney, Agent, or Firm* — Sterne, Kessler, Goldstein & Fox PLLC

(57) ABSTRACT

The novel active compound combinations comprising 2-[2-(1-chlorocyclopropyl)-3-(2-chlorophenyl)-2-hydroxypropyl]-2,4-dihydro-[1,2,4]-triazole-3-thione of the formula

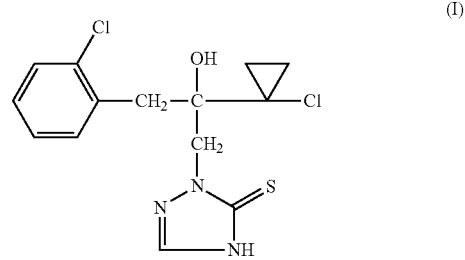

(I)

and the active compound of groups (1) to (24) listed in the description have very good fungicidal properties.

12 Claims, No Drawings

(51) Int. Cl.
| | | |
|---|---|---|
| *A01N 53/00* | (2006.01) | |
| *A01N 43/82* | (2006.01) | |
| *A01N 57/12* | (2006.01) | |
| *A01N 43/88* | (2006.01) | |
| *A01N 37/20* | (2006.01) | |
| *A01N 37/18* | (2006.01) | |
| *A01N 37/22* | (2006.01) | |
| *A01N 43/38* | (2006.01) | |
| *A01N 43/84* | (2006.01) | |
| *A01N 55/02* | (2006.01) | |
| *A01N 47/44* | (2006.01) | |

(56) References Cited

U.S. PATENT DOCUMENTS

| | | |
|---|---|---|
| 3,952,002 A | 4/1976 | Kramer et al. |
| 4,048,318 A | 9/1977 | Meiser et al. |
| 4,127,673 A | 11/1978 | Yamada et al. |
| 4,147,791 A | 4/1979 | Meiser et al. |
| 4,532,341 A | 7/1985 | Holmwood et al. |
| 4,626,595 A | 12/1986 | Holmwood et al. |
| 4,705,800 A | 11/1987 | Nyfeler et al. |
| 4,723,984 A | 2/1988 | Holmwood et al. |
| 4,780,551 A | 10/1988 | Nyfeler et al. |
| 4,789,672 A | 12/1988 | Holmwood et al. |
| 4,871,390 A | 10/1989 | Holmwood et al. |
| 4,904,298 A | 2/1990 | Holmwood et al. |
| 4,910,200 A | 3/1990 | Curtze et al. |
| 4,911,746 A | 3/1990 | Holmwood et al. |
| 4,925,840 A | 5/1990 | Nyfeler et al. |
| 4,931,560 A | 6/1990 | Hubele |
| 4,931,581 A | 6/1990 | Schurter et al. |
| 4,988,734 A | 1/1991 | Kraatz et al. |
| 4,992,438 A | 2/1991 | Ito et al. |
| 5,059,623 A | 10/1991 | Krüger et al. |
| 5,112,849 A | 5/1992 | Staub et al. |
| 5,153,200 A | 10/1992 | Hubele |
| 5,190,928 A | 3/1993 | Schurter et al. |
| 5,304,572 A | 4/1994 | Michelotti et al. |
| 5,334,607 A | 8/1994 | Sauter et al. |
| 5,453,531 A | 9/1995 | Seitz et al. |
| 5,523,311 A | 6/1996 | Schurter et al. |
| 5,599,828 A | 2/1997 | Zeun et al. |
| 5,789,430 A * | 8/1998 | Jautelat et al. ............... 514/384 |
| 5,859,039 A | 1/1999 | Jautelat et al. |
| 5,998,455 A | 12/1999 | Knauf-Beiter et al. |
| 6,103,717 A | 8/2000 | Heinemann et al. |
| 6,297,236 B1 | 10/2001 | Stenzel et al. |
| 6,306,850 B1 | 10/2001 | Dutzmann et al. |
| 6,355,634 B1 | 3/2002 | Isenring et al. |
| 6,407,100 B1 | 6/2002 | Isenring et al. |
| 6,602,823 B1 | 8/2003 | Röchling et al. |
| 6,620,822 B1 | 9/2003 | Dutzmann et al. |
| 6,624,183 B2 | 9/2003 | Wachendorff-Neumann et al. |
| 7,655,599 B2 | 2/2010 | Rochling et al. |
| 8,846,738 B2 * | 9/2014 | Dutzmann et al. ........... 514/384 |
| 2002/0173529 A1 | 11/2002 | Dutzmann et al. |
| 2005/0101639 A1 | 5/2005 | Ammermann et al. |
| 2005/0165076 A1 | 7/2005 | Ammermann et al. |
| 2006/0004070 A1 | 1/2006 | Wachendorff-Neumann et al. |
| 2006/0014738 A1 | 1/2006 | Wachendorff-Neumann et al. |
| 2006/0035942 A1 | 2/2006 | Wachendorff-Neumann et al. |
| 2007/0037799 A1 | 2/2007 | Dahmen et al. |
| 2007/0054804 A1 | 3/2007 | Suty-Heinze |
| 2007/0060579 A1 | 3/2007 | Wachendorff-Neumann et al. |
| 2007/0293550 A1 | 12/2007 | Rochling et al. |
| 2007/0298966 A1 | 12/2007 | Fischer et al. |
| 2008/0139389 A1 | 6/2008 | Kneen et al. |
| 2008/0269051 A1 | 10/2008 | Suty-Heinze et al. |
| 2008/0269263 A1 | 10/2008 | Dahmen et al. |
| 2009/0069178 A1 | 3/2009 | Suty-Heinze et al. |
| 2009/0170918 A1 | 7/2009 | Wolf |
| 2009/0286681 A1 | 11/2009 | Dahmen et al. |
| 2009/0306109 A1 | 12/2009 | Dutzmann et al. |
| 2011/0033433 A1 | 2/2011 | Davies et al. |
| 2011/0034496 A1 | 2/2011 | Häuser-Hahn et al. |
| 2011/0064827 A1 | 3/2011 | Seitz et al. |

FOREIGN PATENT DOCUMENTS

| | | |
|---|---|---|
| WO | WO 96/16048 A1 | 5/1996 |
| WO | WO 9616048 A1 * | 5/1996 |

OTHER PUBLICATIONS

Bauer, T.A., et al., "Response of Selected Weed Species to Postemergence Imazethapyr and Bentazon," *Weed Tech.* 9:236-242, The Weed Science Society of America, United States (1995).

Blackshaw, R.E., "HOE-39866 Use in Chemical Fallow Systems," *Weed Tech.* 3:420-428, The Weed Science Society of America, United States (1989).

Blackshaw, R.E., "Synergistic Mixes of DPX-A7881 and Clopyralid in Canola (*Brassica napus*)," *Weed Tech.* 3:690-695, The Weed Science Society of America, United States (1989).

Blackshaw, R.E., et al., "Herbicide Combinations for Postemergent Weed Control in Safflower (*Carthamus tinctorius*)," *Weed Tech.* 4:97-104, The Weed Science Society of America, United States (1990).

Blouin, D.C., et al., "Analysis of Synergistic and Antagonistic Effects of Herbicides Using Nonlinear Mixed-Model Methodology," *Weed Tech.* 18:464-472, The Weed Science Society of America, United States (2004).

Bradley, P.R., et al., "Response of Sorghum (*Sorghum bicolor*) to Atrazine, Ammonium Sulfate, and Glyphosate," *Weed Tech.* 14:15-18, The Weed Science Society of America, United States (2000).

Buker, III, R.S., et al., "Confirmation and Control of a Paraquat-Tolerant Goosegrass (*Eleusine indica*) Biotype," *Weed Tech.* 16:309-313, The Weed Science Society of America, United States (2002).

Burke, I.C., et al., "CGA-362622 Antagonizes Annual Grass Control with Clethodim," *Weed Tech.* 16:749-754, The Weed Science Society of America, United States (2002).

Flint, J.L., et al., "Analyzing Herbicide Interactions, a Statistical Treatment of Colby's Method," *Weed Tech.* 2:304-309, The Weed Science Society of America, United States (1988).

Gillespie, G.R., and Nalewaja, J.D., "Wheat (*Triticum aestivum*) Response to Triallate Plus Chlorsulfuron," *Weed Tech.* 3:20-23, The Weed Science Society of America, United States (1989).

Green, J.M., et al., "Metribuzin and Chiorimuron Mixtures for Preemergence Broadleaf Weed Control in Soybeans, *Glycine max*," *Weed Tech.* 2:355-363, The Weed Science Society of America, United States (1988).

Harker, N.K., and O'Sullivan, P.A., "Synergistic Mixtures of Sethoxydim and Fluazifop on Annual Grass Weeds," *Weed Tech.* 5:310-316, The Weed Science Society of America, United States(1991).

Kent, L.M., et al., "Effect of Ammonium Sulfate, Imazapyr, and Environment on the Phytotoxicity of Imazethapyr," *Weed Tech.* 5:202-205, The Weed Science Society of America, United States (1991).

Kotoula-Syka, E., et al., "Interactions between SAN 582H and Selected Safeners on Grain Sorghum (*Sorghum bicolor*) and Corn (*Zea mays*)," *Weed Tech.* 10:299-304, The Weed Science Society of America, United States (1996).

Lanclos, D.Y., et al., "Glufosinate Tank-Mix Combinations in Glufosinate-Resistant Rice (*Oryza sativa*)," *Weed Tech.* 16:659-663, The Weed Science Society of America, United States (2002).

Norris, J.L., et al., "Weed Control from Herbicide Combinations with Three Formulations of Glyphosate," *Weed Tech.* 15:552-558, The Weed Science Society of America, United States (2001).

Novosel, K.M., et al., "Metolachlor Efficacy as Influenced by Three Acetolactate Synthase-Inhibiting Herbicides," *Weed Tech.* 12:248-253, The Weed Science Society of America, United States (1998).

Palmer, E.W., et al., "Broadleaf Weed Control in Soybean (*Glycine max*) with CGA-277476 and Four Postemergence Herbicides," *Weed Tech.* 14:617-623, The Weed Science Society of America, United States (2000).

(56) References Cited

OTHER PUBLICATIONS

Salzman, F.P., and Renner, K.A., "Response of Soybean Combinations of Clomazone, Metribuzin, Linuron, Alachlor, and Atrazine," *Weed Tech.* 6:922-929, The Weed Science Society of America, United States (1992).

Scott, R.C., et al., "Spray Adjuvant, Formulation, and Environmental Effects of Synergism from Post-Applied Tank Mixtures of SAN 582H with Fluazifop-P, Imazethapyr, and Sethoxydim," *Weed Tech.* 12:463-469, The Weed Science Society of America, United States (1998).

Shaw, D.R. and Arnold, J.C., "Weed Control from Herbicide Combinations with Glyphosate," *Weed Tech.* 16:1-6, The Weed Science Society of America, United States (2002).

Snipes, C.E., and Allen, R.L., "Interaction of Graminicides Applied in Combination with Pyrithiobac," *Weed Tech.* 10:889-892, The Weed Science Society of America, United States (1996).

Wehtje, G. and Walker, R.N., "Interaction of Glyphosate and 2,4-DB for the Control of Selected Morningglory (*Ipomoea* spp.) Species," *Weed Tech.* 11:152-156, The Weed Science Society of America, United States (1997).

Zhang, W., et al., "Fenoxaprop Interactions for Barnyardgrass (*Echinochloa crus-galli*) Control in Rice," *Weed Tech.* 19:293-297, The Weed Science Society of America, United States (2005).

Colby, S.R., "Calculating synergistic and antagonistic responses of herbicide Combinations," *Weeds* 15:20-22, Weed Science Society of America, United States (1967).

Tomlin, C., ed., *The Pesticide Manual*, Eleventh Edition, 1242-1245, British Crop Protection Council, Farnham, UK (1997).

Opposition Proceeding in European Patent No. EP-B-1482798, Mar. 5, 2007-Nov. 9, 2009.

Prosecution History of European Patent Appl. No. 03735610.2 (European Counterpart of U.S. Appl. No. 10/518,742), Jul. 13, 2006-Sep. 25, 2009.

Partial English language translation of Prosecution History of European Patent Appl. No. 03735610.2, Jul. 13, 2006-Sep. 25, 2009.

Partial English language translation of Opposition Proceeding in European Patent No. EP-B-1482798, Feb. 26, 2007-Nov. 9, 2009.

"Azoxystrobin data sheet," Compendium of Pesticide Common Names, accessed at http://www.alanwood.net/pesticides/azoxystrobin.html, accessed on Apr. 8, 2009, 1 page.

"Kresoxim-methyl data sheet," Compendium of Pesticide Common Names, accessed at http://www.alanwood.net/pesticides/kresoxim-methyl.html, accessed on Apr. 8, 2009, 1 page.

"Metominostrobin data sheet," Compendium of Pesticide Common Names, accessed at http://www.alanwood.net/pesticides/metominostrobin.html, accessed on Apr. 8, 2009, 1 page.

Office Action mailed Nov. 30, 2005, in U.S. Appl. No. 10/518,669, Wachendorff-Neumann et al., filed Jul. 21, 2005.

Office Action mailed Jul. 27, 2006, in U.S. Appl. No. 10/518,669, Wachendorff-Neumann et al., filed Jul. 21, 2005.

Office Action mailed Mar. 22, 2007, in U.S. Appl. No. 10/518,669, Wachendorff-Neumann et al., filed Jul. 21, 2005.

Office Action mailed Oct. 31, 2007, in U.S. Appl. No. 10/518,669, Wachendorff-Neumann et al., filed Jul. 21, 2005.

Office Action mailed May 30, 2008, in U.S. Appl. No. 10/518,669, Wachendorff-Neumann et al., filed Jul. 21, 2005.

Office Action mailed Sep. 15, 2008, in U.S. Appl. No. 10/518,669, Wachendorff-Neumann et al., filed Jul. 21, 2005.

Office Action mailed Mar. 13, 2009, in U.S. Appl. No. 10/518,669, Wachendorff-Neumann et al., filed Jul. 21, 2005.

Office Action mailed Nov. 20, 2009, in U.S. Appl. No. 10/518,669, Wachendorff-Neumann et al., filed Jul. 21, 2005.

Office Action mailed May 25, 2010, in U.S. Appl. No. 10/518,669, Wachendorff-Neumann et al., filed Jul. 21, 2005.

Office Action mailed Jan. 21, 2011, in U.S. Appl. No. 10/518,669, Wachendorff-Neumann et al., filed Jul. 21, 2005.

Office Action mailed Mar. 5, 2009, in U.S. Appl. No. 10/565,883, Dahmen et al., filed May 24, 2006.

Office Action mailed Aug. 31, 2009, in U.S. Appl. No. 10/565,883, Dahmen et al., filed May 24, 2006.

Office Action mailed Apr. 7, 2010, in U.S. Appl. No. 10/565,883, Dahmen et al., filed May 24, 2006.

Office Action mailed Apr. 1, 2009, in U.S. Appl. No. 10/570,945, Suty-Heinze et al., filed Oct. 3, 2006.

Office Action mailed Oct. 20, 2009, in U.S. Appl. No. 10/570,945, Suty-Heinze et al., filed Oct. 3, 2006.

Office Action mailed Feb. 22, 2010, in U.S. Appl. No. 10/570,945, Suty-Heinze et al., filed Oct. 3, 2006.

Office Action mailed Jul. 21, 2010, in U.S. Appl. No. 10/570,945, Suty-Heinze et al., filed Oct. 3, 2006.

Rummens, F.H.A., "An Improved Definition of Synergistic and Antagonistic Effects," *Weed Sci.* 23:4-6, Weed Science Society of America, United States (1975).

Office Action mailed Jul. 20, 2011, in U.S. Appl. No. 10/518,669, Wachendorff-Neumann et al., §371(c) Date: Jul. 21, 2005, U.S. Patent and Trademark Office, Alexandria, VA.

Office Action mailed Aug. 12, 2011, in U.S. Appl. No. 10/570,945, Suty-Heinze et al., § 371(c) Date: Oct. 3, 2006, U.S. Patent and Trademark Office, Alexandria, VA.

Office Action mailed Jun. 17, 2004, for U.S. Appl. No. 09/843,396, inventors: Dutzmann et al., filed Apr. 26, 2001, U.S. Patent and Trademark Office, Alexandria, VA.

Office Action mailed Mar. 24, 2005, for U.S. Appl. No. 09/843,396, inventors: Dutzmann et al., filed Apr. 26, 2001, U.S. Patent and Trademark Office, Alexandria, VA.

Office Action mailed Jul. 25, 2006, for U.S. Appl. No. 09/843,396, inventors: Dutzmann et al., filed Apr. 26, 2001, U.S. Patent and Trademark Office, Alexandria, VA.

Office Action mailed Dec. 28, 2007, for U.S. Appl. No. 09/843,396, inventors: Dutzmann et al., filed Apr. 26, 2001, U.S. Patent and Trademark Office, Alexandria, VA.

Office Action mailed Oct. 6, 2008, for U.S. Appl. No. 09/843,396, inventors: Dutzmann et al., filed Apr. 26, 2001, U.S. Patent and Trademark Office, Alexandria, VA.

Office Action mailed Jun. 8, 2010, for U.S. Appl. No. 09/843,396, inventors: Dutzmann et al., filed Apr. 26, 2001, U.S. Patent and Trademark Office, Alexandria, VA.

Office Action mailed Nov. 23, 2010, for U.S. Appl. No. 09/843,396, inventors: Dutzmann et al., filed Apr. 26, 2001, U.S. Patent and Trademark Office, Alexandria, VA.

Office Action mailed May 24, 2011, for U.S. Appl. No. 09/843,396, inventors: Dutzmann et al., filed Apr. 26, 2001, U.S. Patent and Trademark Office, Alexandria, VA.

Patent Trial and Appeal Board Decision on Appeal mailed Nov. 15, 2012, for U.S. Appl. No. 09/843,396, inventors: Dutzmann et al., filed Apr. 26, 2001, U.S. Patent and Trademark Office, Alexandria, VA.

Office Action mailed Mar. 26, 2013, for U.S. Appl. No. 10/565,883, inventors: Dahmen et al., filed May 24, 2006, U.S. Patent and Trademark Office, Alexandria, VA.

* cited by examiner

FUNGICIDE ACTIVE SUBSTANCE COMBINATIONS

The present invention relates to novel active compound combinations which consist of the known 2-[2-(1-chlorocyclopropyl)-3-(2-chlorophenyl)-2-hydroxypropyl]-2,4-dihydro-[1,2,4]-triazole-3-thione and further known fungicidally active compounds, and which are highly suitable for controlling phytopathogenic fungi.

It is already known that 2-[2-(1-chlorocyclopropyl)-3-(2-chlorophenyl)-2-hydroxypropyl]-2,4-dihydro-[1,2,4]-triazole-3-thione has fungicidal properties (cf. WO 96-16 048). The activity of this compound is good, however, at low application rates it is in some cases not satisfactory.

Furthermore, it is already known that a large number of triazole derivatives, aniline derivatives, dicarboximides and other heterocycles can be employed for controlling fungi (cf. EP-A 0 040 345, DE-A 2 201 063, DE-A 2 324 0 10, Pesticide Manual, 9th Edition (1991), pages 249 and 827, U.S. Pat. No. 3,903,090 and EP-A 0 206 999). Likewise, the activity of these compounds is not always satisfactory at loss application rates.

Finally, it is also known that 1-[(6-chloro-3-pyridinyl)-methyl]-N-nitro-2-imidazolidineimine can be used for controlling animal pests such as insects (cf. Pesticide Manual, 9th Edition (1991), page 491). However, fungicidal properties have not hitherto been described for this compound.

It has now been found that the novel active compound combinations comprising 2-[2-(1-chlorocyclopropyl)-3-(2-chlorophenyl)-2-hydroxypropyl]-2,4-dihydro-[1,2,4]-triazole-3-thione of the formula

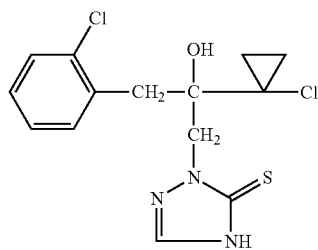

(I)

and
(1) a triazole derivative of the formula

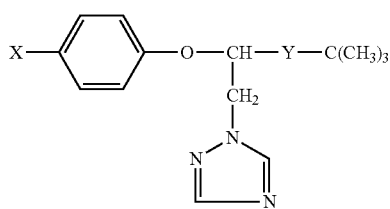

(II)

in which
X represents chlorine or phenyl
and
Y represents

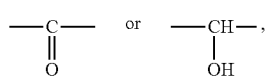

and/or
(2) the triazole derivative of the formula

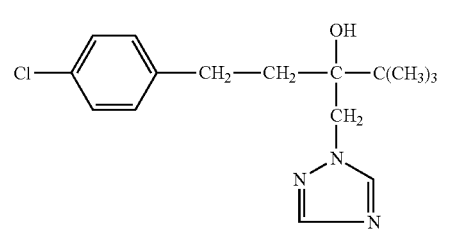

(tebuconazole)

(III)

and/or
(3) an aniline derivative of the formula

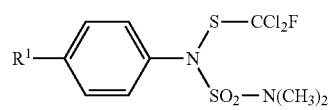

(IV)

in which
$R^1$ represents hydrogen or methyl,
and/or
(4) N-[1-(4-chloro-phenyl)-ethyl]-2,2-dichloro-1-ethyl-3-methyl-cyclopropanecarboxamide of the formula

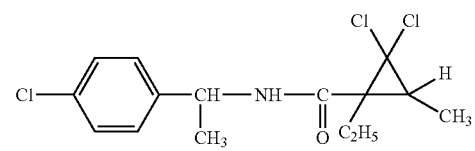

(V)

and/or
(5) the zinc propylene-1,2-bis-(dithiocarbamate) of the formula

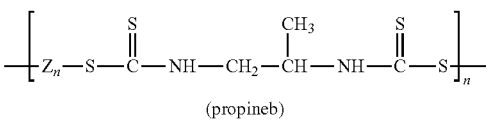

(propineb)

(VI)

n>=1
and/or
(6) at least one thiocarbamate of the formula

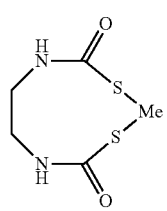

(VII)

Me=Zn or Mn or a mixture of Zn and Mn and/or
(7) the aniline derivative of the formula

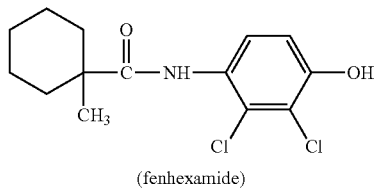

(VIII)

(fenhexamide)

and/or
(8) the compound of the formula

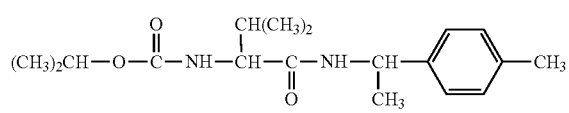

(IX)

and/or
(9) the benzothiadiazole derivative of the formula

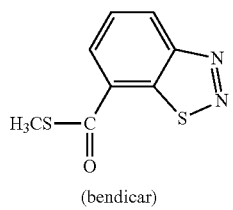

(X)

(bendicar)

and/or
(10) the 8-t-butyl-2-(N-ethyl-N-n-propyl-amino)-methyl-1,4-dioxaspiro-[5,4]-decane of the formula

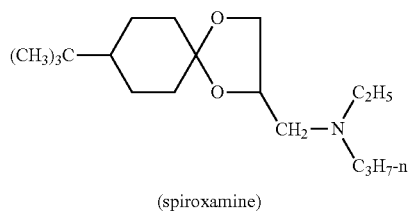

(XI)

(spiroxamine)

and/or
(11) the compound of the formula

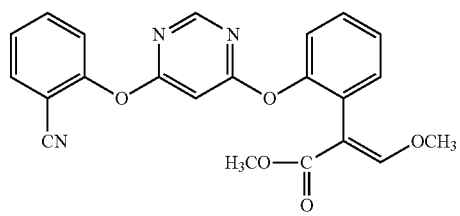

(XII)

(azoxystrobin)

and/or
(12) the compound of the formula

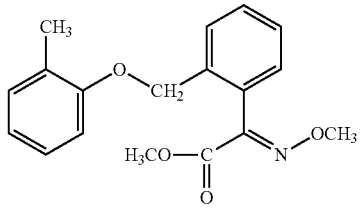

(XIII)

(kresoxim-methyl)

and/or
(13) the compound of the formula

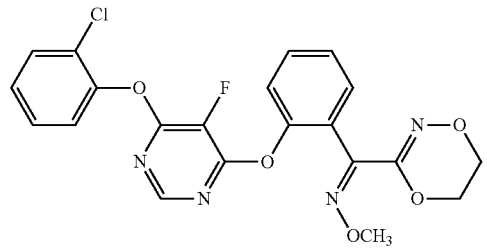

(XIV)

and/or
(14) the dicarboximide of the formula

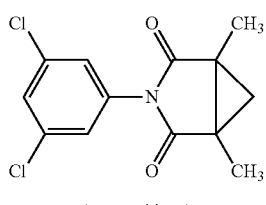

(XV)

(procymidone)

and/or
(15) a pyrimidine derivative of the formula

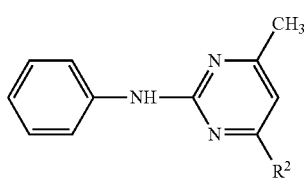

(XVI)

in which $R^2$ represents methyl or cyclopropyl, and/or
(16) the phenyl derivative of the formula

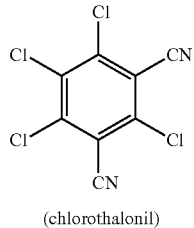

(chlorothalonil)

and/or
(17) the morpholine derivative of the formula

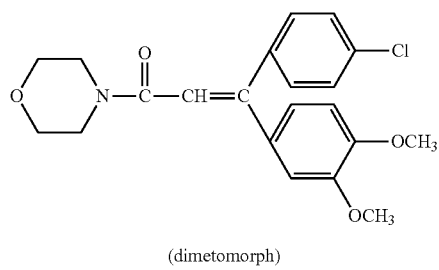

(dimetomorph)

and/or
(18) the phthalimide derivative of the formula

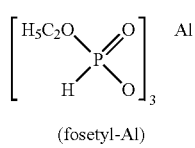

(folpet)

and/or
(19) the phosphorus compound of the formula

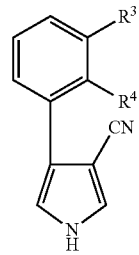

(fosetyl-Al)

and/or
(20) a phenylpyrrole derivative of the formula

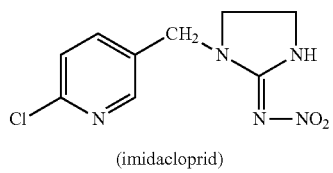

(XXI)

in which
$R^3$ and $R^4$ each represent chlorine or together represent a radical of the formula —O—CF$_2$—O—, and/or
(21) the 1-[(6-chloro-3-pyridinyl)-methyl]-N-nitro-2-imidazolidineimine of the formula (XXII)

(imidacloprid)

and/or
(22) the phenylurea derivative of the formula

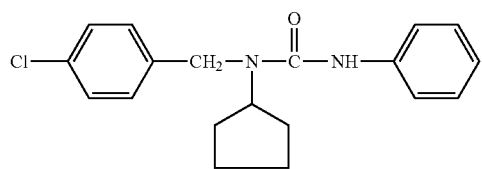

(XXIII)

(pencycuron)

and/or
(23) the benzamide derivative of the formula

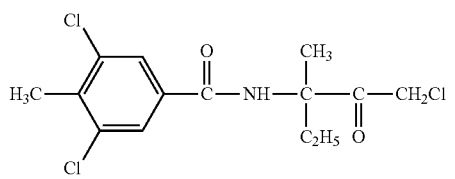

(XXIV)

and/or
(24) a guanidine derivative of the formula

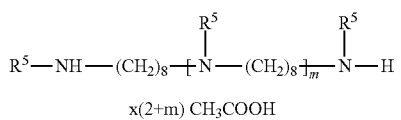

(XXV)

x(2+m) CH$_3$COOH (XVII)

(XVIII)

(XIX)

(XX)

in which
    m represents integers from 0 to 5
    and
    $R^5$ represents hydrogen (17 to 23%) or the radical of the formula

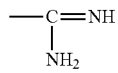

(77 to 83%)

have very good fungicidal properties.

Surprisingly, the fungicidal activity of the active compound combinations according to the invention is considerably higher than the sum of the activities of the individual active compounds. Thus, an unforeseeable, true synergistic effect is present, and not just an addition of activities.

The 2-[2-(1-chlorocyclopropyl)-3-(2-chlorophenyl)-2-hydroxypropyl]-2,4-dihydro-[1,2,4]-triazole-3-thione of the formula (I) is known (cf. WO 96-16 048). The compound can be present in the "thiono" form of the formula

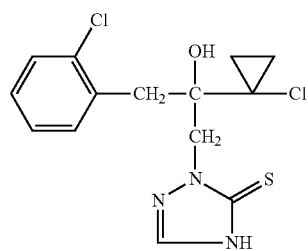

(I)

or in the tautomeric "mercapto" form of the formula

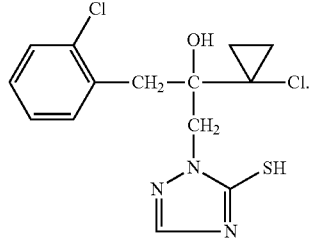

(Ia)

For simplicity's sake, only the "thiono" form is given in each case.

The formula (II) includes the compounds 1-(4-chloro-phenoxy)-3,3-dimethyl-1-(1,2,4-triazol-1-yl)-butane-2-one of the formula

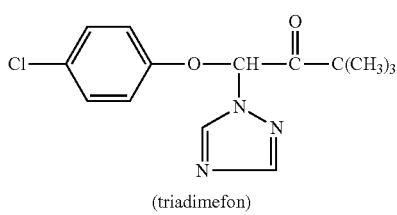

(triadimefon)

1-(4-chloro-phenoxy)-3,3-dimethyl-1-(1,2,4-triazol-1-yl)-butan-2-ol of the formula

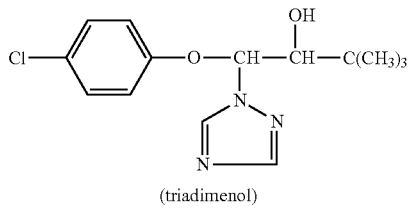

(IIb)

(triadimenol)

and 1-(4-phenyl-phenoxy)-3,3-dimethyl-1-(1,2,4-triazol-1-yl)-butan-2-ol of the formula

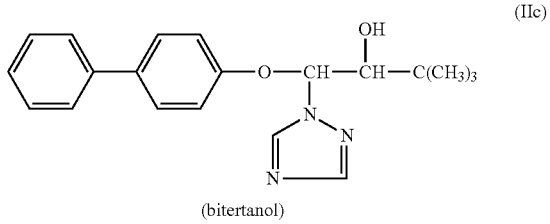 [SMILES: CC(C)(C)C(O)C(Oc1ccc(-c2ccccc2)cc1)n1cncn1]

(IIc)

(bitertanol)

The formula (IV) includes the aniline derivatives of the formulae

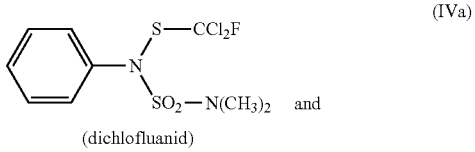

(IVa)

(dichlofluanid)

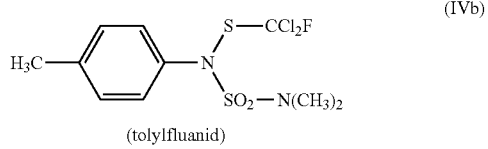

(IVb)

(tolylfluanid)

It is evident from the formula for the active compound of the formula (V) that the compound has three asymmetrically substituted carbon atoms. The product may therefore be present as a mixture of various isomers, or else in the form of a single component. Particular preference is given to the compounds N—(R)-[1-(4-chloro-phenyl)-ethyl]-(1S)-2,2-dichloro-1-ethyl-3t-methyl-1r-cyclopropanecarboxamide of the formula

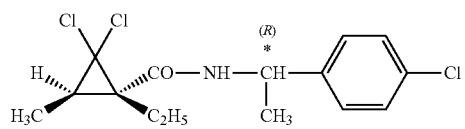

(Va)

and N—(R)-[1-(4-chloro-phenyl)-ethyl]-(1R)-2,2-dichloro-1-ethyl-3t-methyl-1r-cyclopropanecarboxamide of the formula

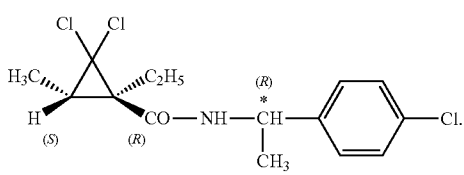 (Vb)

The formula (VII) includes the compounds

Me=Zn (zineb) (VIIa)

Me=Mn (maneb) (VIIb)

and mixture of (VIIa) and (VIIb) (mancozeb). (VIII)

The formula (XVI) includes the compounds $R^2$=CH$_3$ (pyrimethanil) (XVIa)

and

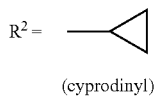 (XVIb)

(cyprodinyl)

The formula (XXI) includes the compounds 4-(2,3-dichlorophenyl)-pyrrole-3-carbonitrile of the formula

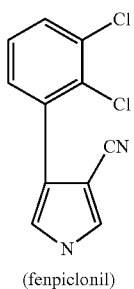 (XXIa)

(fenpiclonil)

and 4-(2,2-difluoro-1,3-benzodioxol-7-yl)-1H-pyrrole-3-carbonitrile of the formula

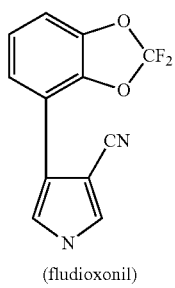 (XXIb)

(fludioxonil)

The guanidine derivative of the formula (XXV) is a mixture of substances of the common name guazatine.

The components which are present in the active compound combinations according to the invention in addition to the active compound of the formula (I) are also known. Specifically, the active compounds are described in the following publications:
(1) Compounds of the formula (II)
DE-A 2 201 063
DE-A 2 324 010
(2) Compound of the formula (III)
EP-A 0 040 345
(3) Compounds of the formula (IV)
Pesticide Manual, 9th Edition (1991), pages 249 and 827
(4) Compound of the formula (V) and individual isomers thereof
EP-A 0 341 475
(5) Compound of the formula (VI)
Pesticide Manual, 9th Edition (1991), page 726
(6) Compounds of the formula (VII)
Pesticide Manual, 9th Edition (1991), pages 529, 531 and 866
(7) Compound of the formula (VIII)
EP-A 0 339 418
(8) Compound of the formula (IX)
EP-A 0 472 996
(9) Compound of the formula (X)
EP-A 0 313 512
(10) Compound of the formula (XI)
EP-A 0 281 842
(11) Compound of the formula (XII)
EP-A 0 382 375
(12) Compound of the formula (XIII)
EP-A 0 515 901
(13) Compound of the formula (XIV)
EP-A 196 02 095
(14) Compound of the formula (XV)
U.S. Pat. No. 3,903,090
(15) Compounds of the formula (XVI)
EP-A 0 270 111
EP-A 0 310 550
(16) Compound of the formula (XVII)
Pesticide Manual, 9th Edition (1991), page 159
(17) Compound of the formula (XVIII)
EP-A 0 219 756
(18) Compound of the formula (XIX)
Pesticide Manual, 9th Edition (1991), page 431
(19) Compound of the formula (XX)
Pesticide Manual, 9th Edition (1991), page 443
(20) Compounds of the formula (XXI)
EP-A 0 236 272
EP-A 0 206 999
(21) Compound of the formula (XXII)
Pesticide Manual, 9th Edition (1991), page 491
(22) Compound of the formula (XXIII)
DE-A 2 732 257
(23) Compound of the formula (XXIV)
EP-A 0 600 629
(24) Substance of the formula (XXV)
Pesticide Manual, 9th Edition (1991), page 461
In addition to the active compound of the formula (I), the active compound combinations according to the invention comprise at least one active compound of the compounds of groups (1) to (24). Additionally, they may comprise further fungicidally active components.

The synergistic effect is particularly pronounced when the active compounds in the active compound combinations according to the invention are present in certain weight ratios. However, the weight ratios of the active compounds in the active compound combinations can be varied within a relatively wide range. In general,
0.1 to 20 parts by weight, preferably 0.2 to 10 parts by weight, of active compound of group (1),
0.1 to 20 parts by weight, preferably 0.2 to 10 parts by weight, of active compound of group (2),
0.2 to 150 parts by weight, preferably 1 to 100 parts by weight, of active compound of group (3),
0.1 to 10 parts by weight, preferably 0.2 to 5 parts by weight, of active compound of group (4),
1 to 50 parts by weight, preferably 5 to 20 parts by weight, of active compound of group (5),
1 to 50 parts by weight, preferably 2 to 20 parts by weight, of active compound of group (6),
0.1 to 50 parts by weight, preferably 1 to 30 parts by weight, of active compound of group (7),
0.2 to 50 parts by weight, preferably 1 to 20 parts by weight, of active compound of group (8),
0.02 to 50 parts by weight, preferably 0.2 to 10 parts by weight, of active compound of group (9),
0.1 to 50 parts by weight, preferably 0.2 to 20 parts by weight, of active compound of group (10),
0.1 to 50 parts by weight, preferably 0.2 to 20 parts by weight, of active compound of group (11),
0.1 to 50 parts by weight, preferably 0.2 to 20 parts by weight, of active compound of group (12),
0.1 to 50 parts by weight, preferably 0.2 to 20 parts by weight, of active compound of group (13),
0.1 to 50 parts by weight, preferably 1 to 30 parts by weight, of active compound of group (14),
0.1 to 50 parts by weight, preferably 0.2 to 20 parts by weight, of active compound of group (15),
0.1 to 50 parts by weight, preferably 2 to 20 parts by weight, of active compound of group (16),
1 to 20 parts by weight, preferably 2 to 10 parts by weight, of active compound of group (17),
1 to 50 parts by weight, preferably 2 to 20 parts by weight, of active compound of group (18),
1 to 50 parts by weight, preferably 2 to 20 parts by weight, of active compound of group (19),
0.1 to 10 parts by weight, preferably 0.2 to 5 parts by weight, of active compound of group (20),
0.05 to 20 parts by weight, preferably 0.1 to 10 parts by weight, of active compound of group (21),
0.1 to 10 parts by weight, preferably 0.2 to 5 parts by weight, of active compound of group (22),
0.1 to 10 parts by weight, preferably 0.2 to 5 parts by weight, of active compound of group (23),
and/or
0.1 to 10 parts by weight, preferably 0.2 to 5 parts by weight, of active compound of group (24)
are present per part by weight of active compound of the formula (I).

The active compound combinations according to the invention have very good fungicidal properties and can be employed for controlling phytopathogenic fungi, such as Plasmodiophoromycetes, Oomycetes, Chytridiomycetes, Zygomycetes, Ascomycetes, Basidiomycetes, Deuteromycetes, etc.

The active compound combinations according to the invention are particularly suitable for controlling cereal diseases, such as *Erysiphe*, *Puccinia* and *Fusarium*, and for controlling diseases encountered in viticulture, such as *Uncinula*, *Plasmopara* and *Botrytis*, and furthermore in dicotyledonous crops for controlling powdery and downy mildew fungi and causative organisms of leaf spot.

The fact that the active compound combinations are well tolerated by plants at the concentrations required for controlling plant diseases permits the treatment of above-ground parts of plants, of propagation stock and seeds, and of the soil. The active compound combinations according to the invention can be employed for foliar application or else as seed dressings.

The active compound combinations according to the invention can be converted to the customary formulations, such as solutions, emulsions, suspensions, powders, foams, pastes, granules, aerosols and microencapsulations in polymeric substances and in coating compositions for seeds, and ULV formulations.

These formulations are produced in a known manner, for example by mixing the active compounds or active compound combinations with extenders, that is liquid solvents, liquefied gases under pressure, and/or solid carriers, optionally with the use of surfactants, that is emulsifiers and/or dispersants, and/or foam formers. If the extender used is water, it is also possible to use, for example, organic solvents as auxiliary solvents. Essentially, suitable liquid solvents include: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at ambient temperature and under atmospheric pressure, for example aerosol propellants such as butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkyl-sulphonates, alkyl sulphates, arylsulphonates, or else protein hydrolysates. Suitable dispersants are: for example ligninsulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and prussian blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compounds, preferably between 0.5 and 90%.

In the formulations, the active compound combinations according to the invention can be present as a mixture with other known active compounds such as fungicides, insecticides, acaricides and herbicides, and as mixtures with fertilizers or plant growth regulators.

The active compound combinations can be used as such, in the form of their formulations or as the use forms prepared therefrom, such as ready-to-use solutions, emulsifiable concentrates, emulsions, suspensions, wettable powders, soluble powders and granules. They are used in the customary manner, for example by watering, spraying, atomizing, scattering, spreading, and as a powder for dry seed treatment, a solution for seed treatment, a water-soluble powder for seed treatment, a water-soluble powder for slurry treatment, or by encrusting.

When using the active compound combinations according to the invention, the application rates can be varied within a relatively wide range, depending on the kind of application. In the treatment of parts of plants, the application rates of the active compound combination are generally between 0.1 and 10,000 g/ha, preferably between 10 and 1000 g/ha. In the treatment of seeds, the application rates of the active compound combination are generally between 0.001 and 50 g per kilogram of seed, preferably between 0.01 and 10 g per kilogram of seed. In the treatment of the soil, the application rates of the active compound combination are generally between 0.1 and 10,000 g/ha, preferably between 1 and 5000 g/ha.

The good fungicidal activity of the active compound combinations according to the invention is evident from the examples below. While the individual active compounds exhibit weaknesses with regard to the fungicidal activity, the combinations have an activity which exceeds a simple addition of activities.

A synergistic effect of fungicides is always present when the fungicidal activity of the active compound combinations exceeds the total of the activities of the active compounds when applied individually.

The expected activity for a given combination of two active compounds can be calculated as follows (cf. Colby, S. R., "Calculating Synergistic and Antagonistic Responses of Herbicide Combinations", Weeds 15, (1967), 20-22).

If

X is the efficacy when applying active compound A at an application rate of m g/ha, Y is the efficacy when applying active compound B at an application rate of n g/ha and E is the efficacy when applying the active compounds A and B at an application rate of m and n g/ha, then $$E = X + Y - \frac{X \cdot Y}{100}$$

The efficacy is calculated in %. 0% is an efficacy which corresponds to that of the control, whereas an efficacy of 100% means that no infection is observed.

If the actual fungicidal activity exceeds the calculated value, then the activity of the combination is superadditive, i.e. a synergistic effect exists. In this case, the efficacy which was actually observed must be greater than the value for the expected efficacy (E) calculated from the abovementioned formula.

The examples that follow illustrate the invention.

EXAMPLE 1

*Sphaerotheca* Test (Cucumber)/Protective

Solvent: 47 parts by weight of acetone
Emulsifier: 3 parts by weight of alkylaryl polyglycol ether
To produce a suitable preparation of active compound, 1 part by weight of active compound or active compound combination is mixed with the stated amounts of solvent and emulsifier, and the concentrate is diluted with water to the desired concentration, or a commercial formulation of active compound or active compound combination is diluted with water to the desired concentration.

To test for protective activity, young plants are sprayed with the active compound preparation at the stated application rate. After the spray coating has dried on, the plants are inoculated with an aqueous spore suspension of *Sphaerotheca fuliginea*. The plants are then placed in a greenhouse at about 23° C. and a relative atmospheric humidity of about 70%.

Evaluation is carried out 10 days after the inoculation. 0% means an efficacy which corresponds to that of the control, whereas an efficacy of 100% means that no infection is observed.

Active compounds, application rates and test results are shown in the table below.

TABLE 1

| Sphaerotheca test (cucumber)/protective | | |
|---|---|---|
| Active compound Known: | Active compound application rate in g/ha | Efficacy in % |
| 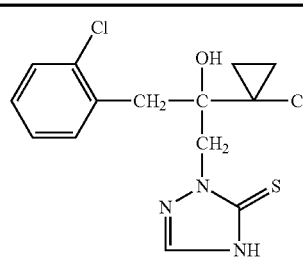 (I) | 2.5 0.5 | 21 0 |

TABLE 1-continued
Sphaerotheca test (cucumber)/protective
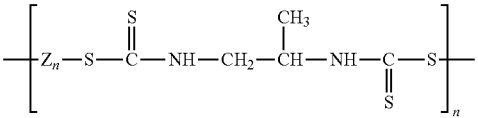
(VI) 25 0
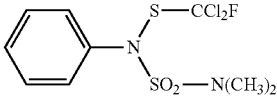
(IVa) 25 0
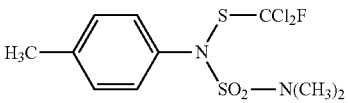
(IVb) 25 0
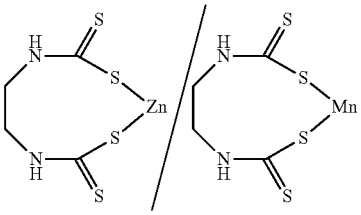
(VIIc) 25 0
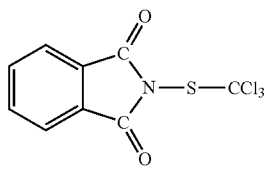
(XIX) 25 0
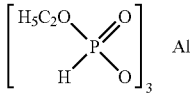
(XX) 50 0
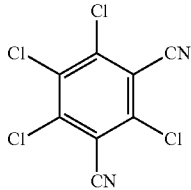 [SMILES: N#Cc1c(Cl)c(Cl)c(Cl)c(C#N)c1Cl]
(XVII) 25 0
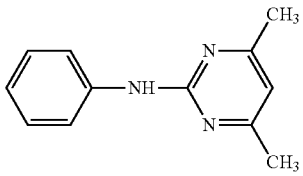
(XVIa) 25 0

TABLE 1-continued

Sphaerotheca test (cucumber)/protective

| Compound | Value 1 | Value 2 |
|---|---|---|
| (XVIb) | 25 | 0 |
| (XXIV) | 12.5 | 0 |
| (XVIII) | 12.5 | 0 |
| (XV) | 12.5 | 0 |
| (VIII) | 12.5 | 0 |
| (XI) | 12.5 | 0 |

TABLE 1-continued

| Sphaerotheca test (cucumber)/protective | | |
|---|---|---|
| (XIII) | 2.5 | 57 |
| (XII) | 2.5 | 59 |
| (IX) | 12.5 | 13 |
| (IIc) | 2.5 | 0 |
| (III) | 2.5 | 50 |
| (IIa) | 2.5 | 37 |

TABLE 1-continued

Sphaerotheca test (cucumber)/protective

| Structure | Application rate | Efficacy |
|---|---|---|
| (IIb) 4-chlorophenoxy-CH(triazolyl)-C(OH)(C(CH₃)₃) | 2.5 | 80 |
| (XIV) pyrimidine derivative with 2-chlorophenoxy, F, and oxime ether groups | 2.5 | 22 |
| (X) bendicar: H₃CS-C(=O)-benzothiadiazole | 2.5 | 0 |

| Active compound According to the invention: | Active compound application rate in g/ha | Efficacy in % found | Efficacy in % calc *) |
|---|---|---|---|
| (I) + (VI) (1:10) | 2.5 + 25 | 70 | 21 |
| (I) + (IVa) (1:10) | 2.5 + 25 | 63 | 21 |
| (I) + (IVb) (1:10) | 2.5 + 25 | 63 | 21 |
| (I) + (VIIc) (1:10) | 2.5 + 25 | 63 | 21 |

TABLE 1-continued

| Sphaerotheca test (cucumber)/protective | | | |
|---|---|---|---|
| (I) + (XIX) (1:10) | 2.5 + 25 | 59 | 21 |
| (I) + (XX) (1:20) | 2.5 + 50 | 52 | 21 |
| (I) + (XVII) (1:10) | 2.5 + 25 | 63 | 21 |
| (I) + (XVIa) (1:10) | 2.5 + 25 | 59 | 21 |
| (I) + (XVIb) (1:10) | 2.5 + 25 | 52 | 21 |
| (I) + (XXIV) (1:5) | 2.5 + 12.5 | 50 | 21 |
| (I) + (XVIII) (1:5) | 2.5 + 12.5 | 63 | 21 |
| (I) + (XV) (1:5) | 2.5 + 12.5 | 50 | 21 |

TABLE 1-continued

| Sphaerotheca test (cucumber)/protective | | | |
|---|---|---|---|
| (I) + (VIII) (1:5) | 2.5 + 12.5 | 75 | 21 |
| (I) + (XI) (1:5) | 2.5 + 12.5 | 54 | 21 |
| (I) + (XIII) (1:5) | 0.5 + 2.5 | 80 | 57 |
| (I) + (XII) (1:5) | 0.5 + 2.5 | 75 | 59 |
| (I) + (IX) (1:5) | 2.5 + 12.5 | 66 | 31 |
| (I) + (IIc) (1:1) | 2.5 + 2.5 | 90 | 21 |
| (I) + (III) (1:1) | 2.5 + 2.5 | 85 | 61 |
| (I) + (IIa) (1:1) | 2.5 + 2.5 | 90 | 50 |

TABLE 1-continued

Sphaerotheca test (cucumber)/protective

| Active compound | | Application rate (g/ha) | | Efficacy (%) found | Efficacy (%) calc. |
|---|---|---|---|---|---|
| (I) + (IIb) (1:1) | | 2.5 + 2.5 | | 93 | 84 |
| (I) + (XIV) (1:1) | | 2.5 + 2.5 | | 70 | 38 |
| (I) + (X) (1:1) | | 2.5 + 2.5 | | 52 | 21 | found = efficacy found
calc. = efficacy calculated using the Colby formula

EXAMPLE 2

Venturia Test (Apple)/Protective

Solvent: 47 parts by weight of acetone
Emulsifier: 3 parts by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration, or a commercial formulation of active compound or active compound combination is diluted with water to the desired concentration.

To test for protective activity, young plants are sprayed with the active compound preparation at the stated application rate. After the spray coating has dried on, the plants are inoculated with an aqueous konidia suspension of the causative organism of apple scab Venturia inaequalis and then remain in an incubation cabin at about 20° C. and 100% relative atmospheric humidity for one day.

The plants are then placed in a greenhouse at about 21° C. and a relative atmospheric humidity of about 90%.

Evaluation is carried out 12 days after the inoculation. 0% means an efficacy which corresponds to that of the control, whereas an efficacy of 100% means that no infection is observed.

Active compounds, application rates and test results are shown in the table below.

TABLE 2

Venturia test (apple)/protective

| Active compound Known: | Active compound application rate in g/ha | Efficacy in % |
|---|---|---|
| 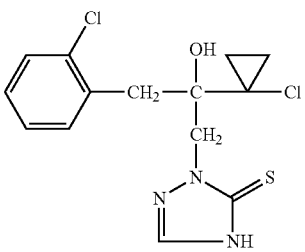 (I) | 1 | 1 |

TABLE 2-continued

Venturia test (apple)/protective

Cl Cl
H⸝⸝⸝ ⸜⸜⸜CO—NH—*CH—⟨C₆H₄⟩—Cl
H₃C C₂H₅ CH₃
(R) (S) (R)

(Va)

+

Cl Cl
H₃C⸝⸝⸝ ⸜⸜⸜C₂H₅
H CO—NH—*CH—⟨C₆H₄⟩—Cl
(S) (R) (R) CH₃

(Vb)

(1:1 mixture)

| Active compound According to the invention: | Active compound application rate in g/ha | Efficacy in % found | calc *) |
|---|---|---|---|
| (I) + (Va/Vb) (1:1) | 1 + 1 | 54 | 1 | found = efficacy found
calc. = efficacy calculated using the Colby formula

EXAMPLE 3

Erysiphe Test (Barley)/Curative

Solvent: 10 parts by weight of N-methyl-pyrrolidone
Emulsifier: 0.6 parts by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration, or a commercial formulation of active compound or active compound combination is diluted with water to the desired concentration.

To test for curative activity, young plants are dusted with spores of *Erysiphe graminis* f. sp. *hordei*. 48 hours after the inoculation, the plants are sprayed with the active compound preparation at the stated application rate.

The plants are placed in a greenhouse at a temperature of about 20° C. and a relative atmospheric humidity of about 80% to promote the development of mildew pustules.

Evaluation is carried out 7 days after the inoculation. 0% means an efficacy which corresponds to that of the control, whereas an efficacy of 100% means that no infection is observed.

Active compounds, application rates and test results are shown in the table below.

TABLE 3

Erysiphe test (barley)/curative

| Active compound | Active compound application rate in g/ha | Efficacy in % |
|---|---|---|
| Known: | | |
| (I) [2-chlorobenzyl-hydroxy-cyclopropyl-chloro-CH₂-triazolethione structure] | 25 | 81 |

TABLE 3-continued

Erysiphe test (barley)/curative

| Active compound | Active compound application rate in g/ha | Efficacy in % |
|---|---|---|
| 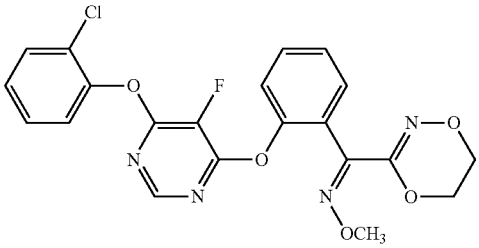 (XIV) | 25 | 75 |
| According to the invention: | | |
| (I) + (XIV) (1:3) | 6.25 + 18.75 | 100 |

EXAMPLE 4

Erysiphe Test (Barley)/Protective

Solvent: 10 parts by weight of N-methyl-pyrrolidone
Emulsifier: 0.6 parts by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration, or a commercial formulation of active compound or active compound combination is diluted with water to the desired concentration.

To test for protective activity, young plants are sprayed with the active compound preparation at the stated application rate.

After the spray coating has dried on, the plants are dusted with spores of *Erysiphe graminis* f. sp. *hordei*.

The plants are placed in a greenhouse at a temperature of about 20° C. and a relative atmospheric humidity of about 80% to promote the development of mildew pustules.

Evaluation is carried out 7 days after the inoculation. 0% means an efficacy which corresponds to that of the control, whereas an efficacy of 100% means that no infection is observed.

Active compounds, application rates and test results are shown in the table below

TABLE 4

Erysiphe test (barley)/curative

| Active compound | Active compound application rate in g/ha | Efficacy in % |
|---|---|---|
| Known: | | |
| 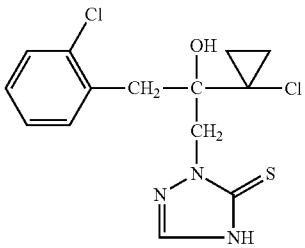 [SMILES: OC(Cc1ccccc1Cl)(Cn1nc[nH]c1=S)C1(Cl)CC1] (I) | 25 | 83 |

TABLE 4-continued

Erysiphe test (barley)/curative

| Active compound | Active compound application rate in g/ha | Efficacy in % |
|---|---|---|
| (XII) [structure: bis-aryloxy pyrimidine with CN and methoxyacrylate substituents] | 25 | 92 |

According to the invention:

| | | |
|---|---|---|
| (I) + (XII) (1:1) | 12.5 + 12.5 | 100 |
| (I) + (XII) (1:3) | 6.25 + 18.75 | 100 |
| (I) + (XII) (3:1) | 18.75 + 6.25 | 100 |

EXAMPLE 5

*Erysiphe* Test (Wheat)/Curative

Solvent: 10 parts by weight of N-methyl-pyrrolidone
Emulsifier: 0.6 parts by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration, or a commercial formulation of active compound or active compound combination is diluted with water to the desired concentration.

To test for curative activity, young plants are dusted with spores of *Erysiphe graminis* f. sp. *tritici*. 48 hours after the inoculation, the plants are sprayed with the active compound preparation at the stated application rate.

The plants are then placed in a greenhouse at a temperature of about 20° C. and a relative atmospheric humidity of about 80% to promote the development of mildew pustules.

Evaluation is carried out 7 days after the inoculation. 0% means an efficacy which corresponds to that of the control, whereas an efficacy of 100% means that no infection is observed.

Active compounds, application rates and test results are shown in the table below.

TABLE 5
| Active compound | Active compound application rate in g/ha | Efficacy in % |
|---|---|---|
| Known: | | |
| 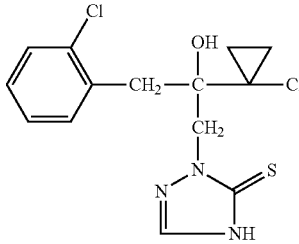 (I) | 25<br>12.5<br>6.25 | 75<br>50<br>25 |
| 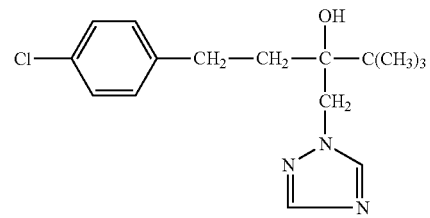 [SMILES: CC(C)(C)C(O)(CCc1ccc(Cl)cc1)Cn1cncn1] (III) | 25 | 88 |
| 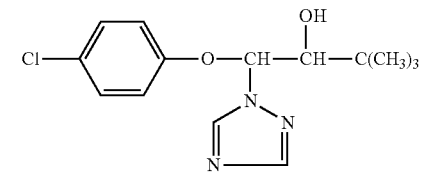 [SMILES: CC(C)(C)C(O)C(Oc1ccc(Cl)cc1)n1cncn1] (IIb) | 25 | 81 |
| 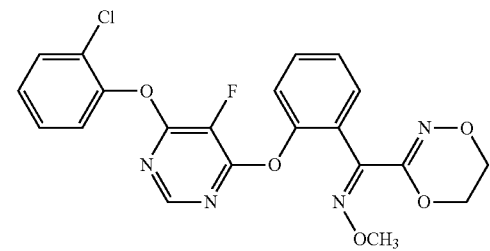 [SMILES: CO/N=C(\C1=NOCCO1)c1ccccc1Oc1ncnc(Oc2ccccc2Cl)c1F] (XIV) | 12.5 | 0 |
| 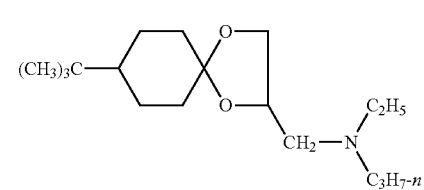 (XI) | 12.5 | 0 |

TABLE 5-continued
Erysiphe test (wheat)/curative
| Active compound | Active compound application rate in g/ha | Efficacy in % |
|---|---|---|
| 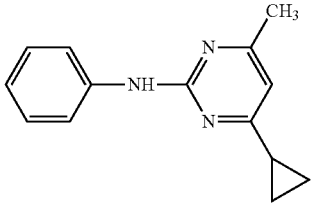 [SMILES: Cc1cc(C2CC2)nc(Nc2ccccc2)n1] (XVIb) | 12.5 | 0 |
| 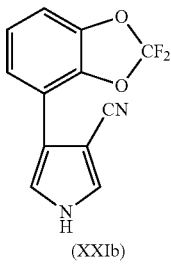 (XXIb) | 6.25 | 38 |
| 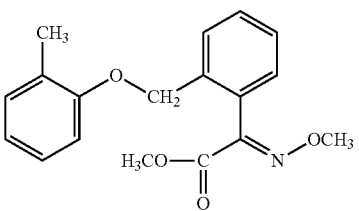 [SMILES: CO/N=C(/C(=O)OC)c1ccccc1COc1ccccc1C] (XIII) | 6.25 | 94 |
According to the invention:
| Active compound | Active compound application rate in g/ha | Efficacy in % |
|---|---|---|
| (I) + (III) (1:1) | 12.5 + 12.5 | 100 |
| (I) + (III) (1:3) | 6.25 + 18.75 | 100 |
| (I) + (III) (3:1) | 18.75 + 6.25 | 100 |
| (I) + (IIb) (1:1) | 12.5 + 12.5 | 100 |

TABLE 5-continued

| Active compound | Active compound application rate in g/ha | Efficacy in % |
|---|---|---|
| (I) + (IIb) (1:3) | 6.25 + 18.75 | 100 |
| (I) + (XIV) (1:1) | 6.25 + 6.25 | 63 |
| (I) + (XIV) (3:1) | 9.375 + 3.125 | 75 |
| (I) + (XI) (1:1) | 6.25 + 6.25 | 100 |
| (I) + (XI) (1:3) | 3.125 + 9.375 | 100 |
| (I) + (XI) (3:1) | 9.375 + 3.125 | 100 |
| (I) + (XXIb) (1:1) | 6.25 + 6.25 | 75 |
| (I) + (XXIb) (1:3) | 1.5625 + 4.6875 | 50 |

TABLE 5-continued

Erysiphe test (wheat)/curative

| Active compound | Active compound application rate in g/ha | Efficacy in % |
|---|---|---|
| (I) + (XIII) (1:1) | 3.125 + 3.125 | 100 |
| (I) + (XIII) (1:3) | 1.5625 + 4.6875 | 100 |

EXAMPLE 6

*Erysiphe* Test (Wheat)/Protective

Solvent: 10 parts by weight of N-methyl-pyrrolidone
Emulsifier: 0.6 parts by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration, or a commercial formulation of active compound or active compound combination is diluted with water to the desired concentration.

To test for protective activity, young plants are sprayed with the active compound preparation at the stated application rate.

After the spray coating has dried on, the plants are dusted with spores of *Erysiphe graminis* f. sp. *tritici*.

The plants are then placed in a greenhouse at a temperature of about 20° C. and a relative atmospheric humidity of about 80% to promote the development of mildew pustules.

Evaluation is carried out 7 days after the inoculation. 0% means an efficacy which corresponds to that of the control, whereas an efficacy of 100% means that no infection is observed.

Active compounds, application rates and test results are shown in the table below.

TABLE 6

Erysiphe test (wheat)/protective

| Active compound | Active compound application rate in g/ha | Efficacy in % |
|---|---|---|
| Known: | | |
| (I) | 6.25 | 57 |
| (III) | 6.25 | 57 |

TABLE 6-continued

Erysiphe test (wheat)/protective

| Active compound | Active compound application rate in g/ha | Efficacy in % |
|---|---|---|
| According to the invention: | | |
| (I) + (III) (1:1) | 3.125 + 3.125 | 79 |
| (I) + (III) (1:3) | 1.5625 + 4.6875 | 71 |
| (I) + (III) (3:1) | 4.6875 + 1.5625 | 71 |

EXAMPLE 7

*Leptosphaeria nodorum* Test (Wheat)/Protective

Solvent: 10 parts by weight of N-methyl-pyrrolidone

Emulsifier: 0.6 parts by weight of alkylaryl polyglycol ether

To produce a suitable preparation of active compound, 1 part by weight of active compound or active compound combination is mixed with the stated amounts of solvent and emulsifier, and the concentrate is diluted with water to the desired concentration, or a commercial formulation of active compound or active compound combination is diluted with water to the desired concentration.

To test for protective activity, young plants are sprayed with the active compound preparation at the stated application rate.

After the spray coating has dried on, the plants are sprayed with a spore suspension of *Leptosphaeria nodorum*. The plants remain in an incubation cabin at 20° C. and 100% relative atmospheric humidity for 48 hours.

The plants are then placed in a greenhouse at a temperature of about 15° C. and a relative atmospheric humidity of about 80%.

Evaluation is carried out 10 days after the inoculation. 0% means an efficacy which corresponds to that of the control, whereas an efficacy of 100% means that no infection is observed.

Active compounds, application rates and test results are shown in the table below.

TABLE 7

Leptosphaeria nodorum test (wheat)/protective

| Active compound | Active compound application rate in g/ha | Efficacy in % |
|---|---|---|
| Known: | | |
| (I) [structure] | 25 | 62 |

TABLE 7-continued

| Leptosphaeria nodorum test (wheat)/protective | | |
|---|---|---|
| Active compound | Active compound application rate in g/ha | Efficacy in % |
| 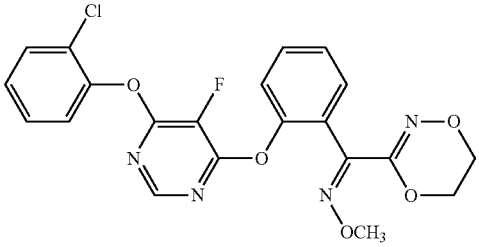 [SMILES: CO/N=C(\C1=NOCCO1)c1ccccc1Oc1ncnc(Oc2ccccc2Cl)c1F]<br>(XIV) | 25 | 87 |
| According to the invention: | | |
| (I) + (XIV) (1:3) | 6.25 + 18.75 | 100 |

EXAMPLE 8

Puccinia Test (Wheat)/Protective

Solvent: 10 parts by weight of N-methyl-pyrrolidone
Emulsifier: 0.6 parts by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration, or a commercial formulation of active compound or active compound combination is diluted with water to the desired concentration.

To test for protective activity, young plants are inoculated with a spore suspension of *Puccinia recondita* in a 0.1% strength aqueous agar solution. After the spray coating had dried on, the plants are sprayed with the active compound preparation at the stated application rate.

The plants remain in an incubation cabin at 20° C. and 100% relative atmospheric humidity for 24 hours.

The plants are then placed in a greenhouse at a temperature of about 20° C. and a relative atmospheric humidity of about 80% to promote the development of rust pustules.

Evaluation is carried out 10 days after the inoculation. 0% means an efficacy which corresponds to that of the control, whereas an efficacy of 100% means that no infection is observed.

Active compounds, application rates and test results are shown in the table below.

TABLE 8

| Puccinia test (wheat)/protective | | |
|---|---|---|
| Active compound | Active compound application rate in g/ha | Efficacy in % |
| Known: | | |
| 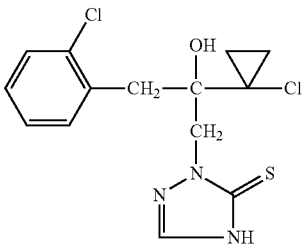<br>(I) | 25 | 38 |

TABLE 8-continued

Puccinia test (wheat)/protective

| Active compound | Active compound application rate in g/ha | Efficacy in % |
|---|---|---|

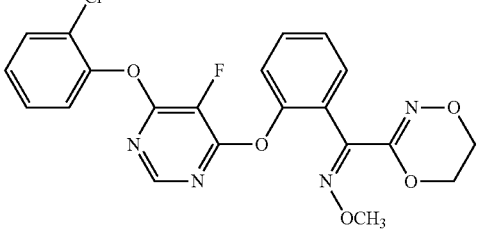

| | 25 | 94 |
|---|---|---|

(XIV)

According to the invention:

| (I) + (XIV) (1:3) | 6.25 + 18.75 | 100 |
|---|---|---|
| (I) + (XIV) (3:1) | 18.75 + 6.25 | 100 |

EXAMPLE 9

Fusarium culmorum Test (Wheat)/Seed Treatment

The active compounds are applied as a dry seed dressing. This is prepared by extending the respective active compound or the active compound combination with ground minerals to give a finely pulverulent mixture which ensures uniform distribution on the seed surface.

To dress the seed, the infected seed together with the seed dressing is shaken for 3 minutes in a sealed glass flask.

2×100 corns of wheat are sown at a depth of 1 cm in standard soil and cultivated in a greenhouse at a temperature of about 18° C. and a relative atmospheric humidity of about 95% in seed trays which receive a light regimen of 15 hours per day.

About 3 weeks after sowing, the plants are evaluated for symptoms. 0% means an efficacy which corresponds to that of the control, whereas an efficacy of 100% means that no infection is observed.

Active compounds, application rates and test results are shown in the table below.

TABLE 9

Fusarium culmorum test (wheat)/seed treatment

| Active compound | Active compound application rate in g/ha | Efficacy in % |
|---|---|---|

Known:

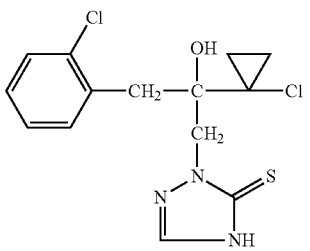 [SMILES: OC(Cc1ccccc1Cl)(Cn1nc[nH]c1=S)C1(Cl)CC1]

| | 75 | 32 |
|---|---|---|

(I)

TABLE 9-continued

Fusarium culmorum test (wheat)/seed treatment

| Active compound | Active compound application rate in g/ha | Efficacy in % |
|---|---|---|
| 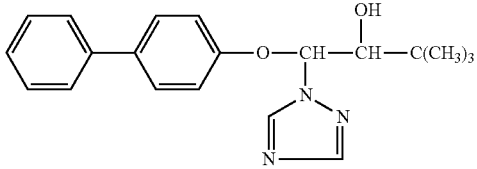 (IIc) | 75 | 27 |
| According to the invention: | | |
| (I) + (IIc) (1:1) | 37.5 + 37.5 | 41 |

EXAMPLE 10

*Fusarium nivale* Test (Triticale)/Seed Treatment

The active compounds are applied as a dry seed dressing. This is prepared by extending the respective active compound or the active compound combination with ground minerals to give a finely pulverulent mixture which ensures uniform distribution on the seed surface.

To dress the seed, the infected seed together with the seed dressing is shaken for 3 minutes in a sealed glass flask.

2×100 corns of wheat are sown at a depth of 1 cm in standard soil and cultivated in a greenhouse at a temperature of about 10° C. and a relative atmospheric humidity of about 95% in seed trays which receive a light regimen of 15 hours per day.

About 3 weeks after sowing, the plants are evaluated for symptoms. 0% means an efficacy which corresponds to that of the control, whereas an efficacy of 100% means that no infection is observed.

Active compounds, application rates and test results are shown in the table below

TABLE 10

Fusarium nivale test (triticale)/seed treatment

| Active compound | Active compound application rate in g/ha | Efficacy in % |
|---|---|---|
| Known: | | |
| 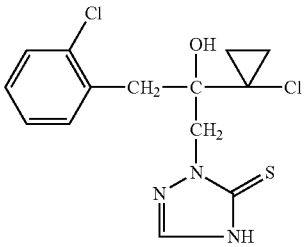 (I) | 75<br>25 | 14<br>0 |
| 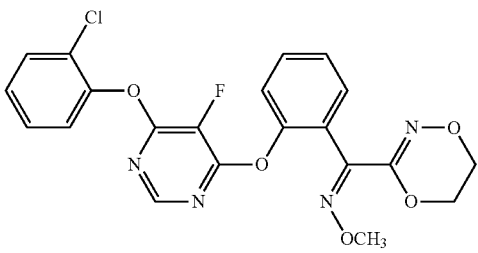 (XIV) | 75 | 94 |

TABLE 10-continued

Fusarium nivale test (triticale)/seed treatment

| Active compound | Active compound application rate in g/ha | Efficacy in % |
|---|---|---|
| 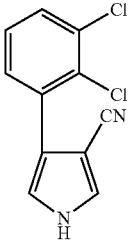 (XXIa) | 25 | 0 |
| According to the invention: | | |
| (I) + (XIV) (1:1) | 37.5 + 37.5 | 99 |
| (I) + (XXIa) (1:1) | 12.5 + 12.5 | 31 |

EXAMPLE 11

Rhizoctonia solani Test (Cotton)/Seed Treatment

The active compounds are applied as a dry seed dressing. This is prepared by extending the respective active compound or the active compound combination with ground minerals to give a finely pulverulent mixture which ensures uniform distribution on the seed surface.

To dress the seed, the infected seed together with the seed dressing is shaken for 3 minutes in a sealed glass flask.

2×50 corns of seed are sown at a depth of 2 cm in standard soil infected with Rhizoctonia solani, and the seeds are cultivated in a greenhouse at a temperature of about 22° C. in seed trays which receive a light regimen of 15 hours per day.

Evaluation is carried out after 8 days. 0% means an efficacy which corresponds to that of the control, whereas an efficacy of 100% means that no infection is observed.

Active compounds, application rates and test results are shown in the table below

TABLE 11

Rhizoctonia solani test (cotton)/seed treatment

| Active compound | Active compound application rate in g/ha | Efficacy in % |
|---|---|---|
| Known: | | |
| 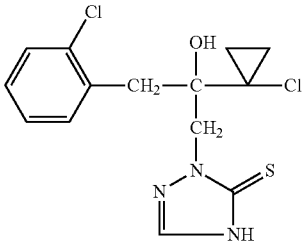 [SMILES: OC(Cc1ccccc1Cl)(Cn1nc[nH]c1=S)C1(Cl)CC1] (I) | 25 | 19 |

TABLE 11-continued

Rhizoctonia solani test (cotton)/seed treatment

| Active compound | Active compound application rate in g/ha | Efficacy in % |
|---|---|---|
| 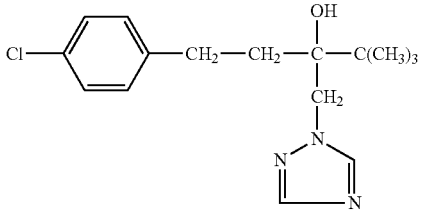 (III) | 25 | 27 |
| 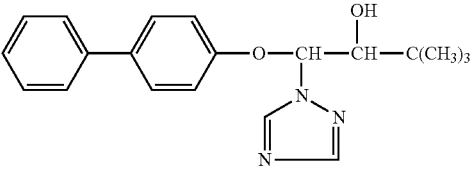 (IIc) | 25 | 0 |
| According to the invention: | | |
| (I) + (III) (1:1) | 12.5 + 12.5 | 40 |
| (I) + (IIc) (1:1) | 12.5 + 12.5 | 31 |

We claim:

1. A fungicidal composition comprising synergistically effective amounts of:
   (a) a 2-[2-(1-chlorocyclopropyl)-3-(2-chlorophenyl)-2-hydroxypropyl]2,4-dihydro-[1,2,4]-triazole-3-thione of the formula

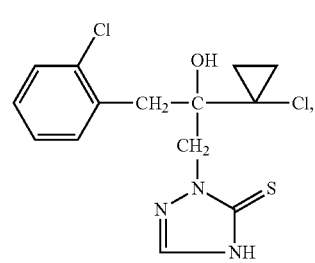

(I)

and (b) a triazole derivative of the formula

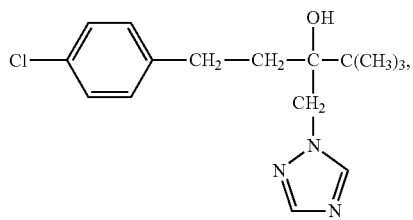

(tebuconazole), wherein the weight ratio of active compound of the formula (I) to the active compound of the formula (III) is from 5:1 to 1:10.

2. A method for controlling fungi comprising applying the composition according to claim 1 to the fungi and/or their habitat.

3. The method according to claim 2 wherein the fungi is a cereal disease.

4. The method according to claim 3 wherein the cereal disease is selected from the group consisting of *Erysiphe, Puccinia*, and *Fusarium*.

5. The method according to claim 2 wherein the composition is applied to plant parts at a rate between 10 and 1000 g/ha.

6. The method according to claim 2 wherein the composition is applied to soil at a rate between 1 and 5000 g/ha.

7. A method for controlling fungi comprising applying a fungicidal composition comprising synergistically effective amounts of:

(a) a 2-[2-(1-chlorocyclopropyl)-3-(2-chlorophenyl)-2-hydroxypropyl]2,4-dihydro-[1,2,4]-triazole-3-thione of the formula

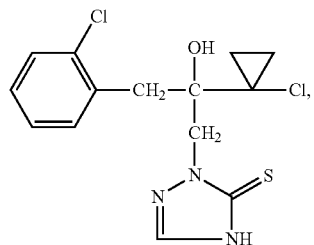

(I)

and (b) a triazole derivative of the formula

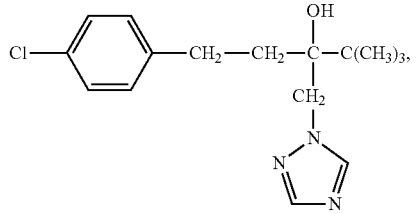

(III)

(tebuconazole), wherein the weight ratio of active compound of the formula (I) to the active compound of the formula (III) is from 5:1 to 1:10.

8. The method according to claim 7 wherein the fungi is a cereal disease.

9. The method according to claim 8 wherein the cereal disease is selected from the group consisting of *Erysiphe, Puccinia*, and *Fusarium*.

10. The method according to claim 7 wherein the composition is applied to plant parts at a rate between 10 and 1000 g/ha.

11. The method according to claim 7 wherein the composition is applied to soil at a rate between 1 and 5000 g/ha.

12. The method according to claim 10 wherein the composition is applied to plant parts at a rate between 25 to 1000 g/ha.

* * * * *